United States Patent [19]

Bergstrom et al.

[11] 4,146,793

[45] Mar. 27, 1979

[54] X-RAY DEVICES USING EPOXY RESINS STRENGTHENED WITH CARBONIC FIBROUS MATERIAL

[75] Inventors: Lennart Bergstrom, Taby; Hans E. Warden, Upplands Vasby, both of Sweden

[73] Assignee: Siemens AG, Munich, Fed. Rep. of Germany

[21] Appl. No.: 675,785

[22] Filed: Apr. 12, 1976

Related U.S. Application Data

[60] Continuation-in-part of Ser. No. 522,229, Nov. 8, 1974, abandoned, which is a division of Ser. No. 382,013, Jul. 23, 1973, abandoned.

[30] Foreign Application Priority Data

Jul. 27, 1972 [DE] Fed. Rep. of Germany ....... 2236942

[51] Int. Cl.$^2$ ............................................. G03B 41/16
[52] U.S. Cl. ................................... 250/444; 250/451; 250/475; 250/439 R
[58] Field of Search ............... 250/439, 444, 445, 446, 250/447, 448, 449, 454, 475, 490

[56] References Cited

U.S. PATENT DOCUMENTS

| | | | |
|---|---|---|---|
| 2,930,305 | 3/1960 | Sullivan | 250/475 |
| 3,449,570 | 6/1969 | Kok | 250/439 |
| 3,897,345 | 7/1975 | Foster | 250/439 |
| 3,947,686 | 3/1976 | Cooper et al. | 250/439 |

OTHER PUBLICATIONS

Phillips; "Carbon–Fibre–Reinforced Plastics"; Trans. J. Plastics Inst., Aug. 1967; pp. 589–593.

*Primary Examiner*—Alfred E. Smith
*Assistant Examiner*—B. C. Anderson
*Attorney, Agent, or Firm*—Allison C. Collard; Thomas M. Galgano

[57] ABSTRACT

Cast resins strengthened with carbonic fibrous material are used as the material for making parts which transmit X-rays and at the same time are subject to mechanical stresses.

13 Claims, 5 Drawing Figures

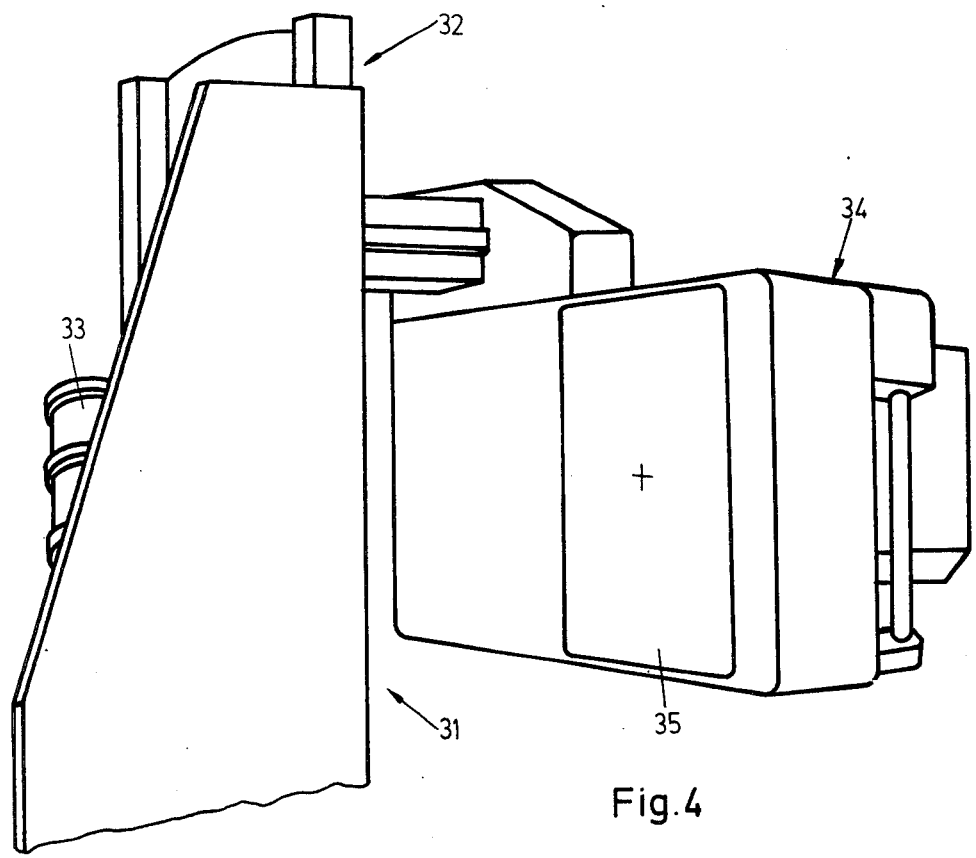
Fig. 4
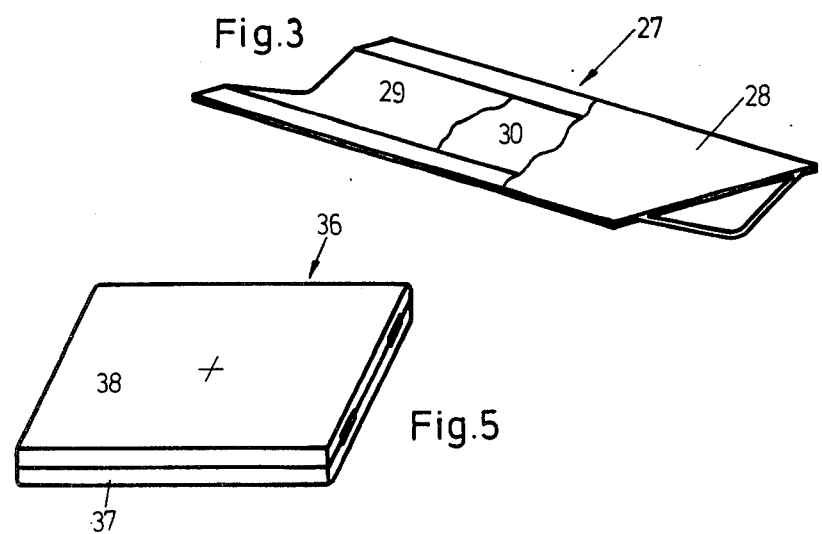
Fig. 3
Fig. 5

X-RAY DEVICES USING EPOXY RESINS STRENGTHENED WITH CARBONIC FIBROUS MATERIAL

The present application is a continuation in part of a co-pending patent applicaton Ser. No. 522,229, filed Nov. 8, 1974 which is a divisional application of prior co-pending application Ser. No. 382,013 filed July 23, 1973 both abandoned.

This invention relates to new uses of cast resins strengthened with carbonic fibrous material.

A synthetic substance having the base of epoxyde synthetic resin is known, the mechanical strength of which is greatly increased by intercalating a carbonic fibrous material. The uses of this new synthetic substance are described at length in the prospectus of the film Fothergill & Harvey Ltd., Composite Materials Division, Littleborough, Lancashire, England, publication No. 27 B 1971, printed in England. These uses were described as advantageous due to the saving in weight, resistance against chemical action and small coefficient of friction. Among others the following uses were indicated: airplane cells, sporting devices, artificial members, rotary parts of centrifuges, rotary sheets, containers, parts of ships, self lubricating bearings and tools.

The present invention is based on extensive experimentation which was actually carried out and which has discovered completely new clearly apparent properties of cast resin strengthened with carbonic fibrous material. Due to these properties the present invention provides the use of these synthetic substances as material for producing parts which transmit X-rays and at the same time are subject to mechanical stresses. This use of the synthetic substance is based on the consideration that in the case of structural elements of specific strength there is an X-ray and gamma ray absorption which is smaller by more then the tenth power than with aluminum. Thus, for example, the X-ray absorption of a plate of epoxyde cast resin strengthened with carbonic fibrous material and having a thickness of 2.5 mm, corresponds to that of an aluminum plate with a thickness of 0.2 mm. The tensile strength per $mm^2$ of this substance is, however, not smaller then that of aluminum but actually greater by the factor 2. The found small X-ray and gamma ray absorption of structural elements made of cast resin strengthened by carbonic fibrous material, therefore cannot be explained solely by the use of thin wall thickness made possible by substantial mechanical strength values. Rather this effect is here increased many times by the particularly small density of the synthetic material and the relatively small ordinal number of all used elements. In addition, the experiments have shown that there is a particularly small induced stray ray portion apparently due to the low ordinal number of elements contained in the synthetic material. Finally all these effects of all these properties which assist each other have produced the discovered particular usefulness of this synthetic material for the above-mentioned uses. Actually epoxide cast resin serves solely for embedding the carbonic fibrous material which is responsive for the particular mechanical and electrical properties. Therefore, instead of the epoxyde cast resin other cast resins can be used provided that they are sufficiently hard.

Actual experimentation has shown that all known epoxyde resins are suitable as matrix for the purpose of the present invention.

According to a particularly advantageous embodiment of the present invention the synthetic material can be used for patient supporting table tops of X-ray apparatus. Such a patient supporting table top must weaken the X-ray illumination as little as possible. Furthermore, the creation of stray rays is most undesirable in X-ray diagnosis since they diminish the contrast upon the image layer and thus make details less visible. In ray therapy stray rays are undesirable since they change the dose distribution in the treating range. The found specific properties of the new synthetic substance thus make it particularly suitable for both uses of the patient supporting table tops.

According to a preferred embodiment of the present invention the synthetic material is used for the supporting surface of a patient carrying table top which is fixed between elongated beams. The properties of the mechanical firmness of the synthetic material are particularly well suited for receiving forces which may be applied to such a supporting surface. This is particularly so when according to a further development of the present invention the supporting surface is curved between the two beams. The binding stresses are diminished by such a curvature of the supporting surface. Due to a particularly great tensile strength of this synthetic substance it is possible to provide in this manner a particularly thin supporting surface of sufficient firmness.

According to a further advantageous embodiment of the present invention the two longitudinal edges of the supporting surface can be provided with thickened pads which are firmly fitted in corresponding grooves provided in the longitudinal beams of the patient supporting table top. This construction of the supporting surface provides a uniform transmission of the supporting forces upon the longitudinal beams. Furthermore, bore holes in the supporting surface are avoided which in the past were necessary for screw connections. This is particularly important since such bore holes spatially divide the carbonic fibrous material and thus the strength is greatly diminished just at the attachment point.

According to a further particularly advantageous embodiment of the present invention the synthetic substance can be used as an upper and a lower covering layer upon a core of hard foam so that the top of the patient supporting plate is like a sandwich. This structure of the patient supporting plate is particularly adapted to the special properties of the synthetic substance with respect to the adhesion to the hard foam core and also in relation to tensile strength.

The strength of such a patient supporting table top having the structure of a sandwich can be further increased when according to a further feature of the present invention the upper and lower covering layers are connected with each other at least at the longitudinal sides of the patient supporting table top.

According to a further advantageous embodiment of the present invention the synthetic substance can be applied to the side of an X-ray image amplifying casing directed toward the source of X-rays. The synthetic substance is particularly suitable for this purpose due to its transparency for X-rays combined with a comparatively high rigidity and due to the very small proportion of stray rays produced by it. For the same reason according to further embodiments of the present invention the synthetic substance is also suitable for the side of an X-ray aiming instrument housing directed toward the X-ray source and for the side of X-ray film cassettes directed to the X-ray source.

The invention will appear more clearly from the following detailed description when taken in connection with the accompanying drawings showing by way of example only, preferred embodiments of the inventive idea.

In the drawings:

FIG. 3 is a perspective view, partly in section, of a patient supporting table top having a foam core.

FIG. 4 is a perspective view of an X-ray examining apparatus with an X-ray aiming device.

FIG. 5 is a perspective view of an X-ray film cassette.

Figure 1:
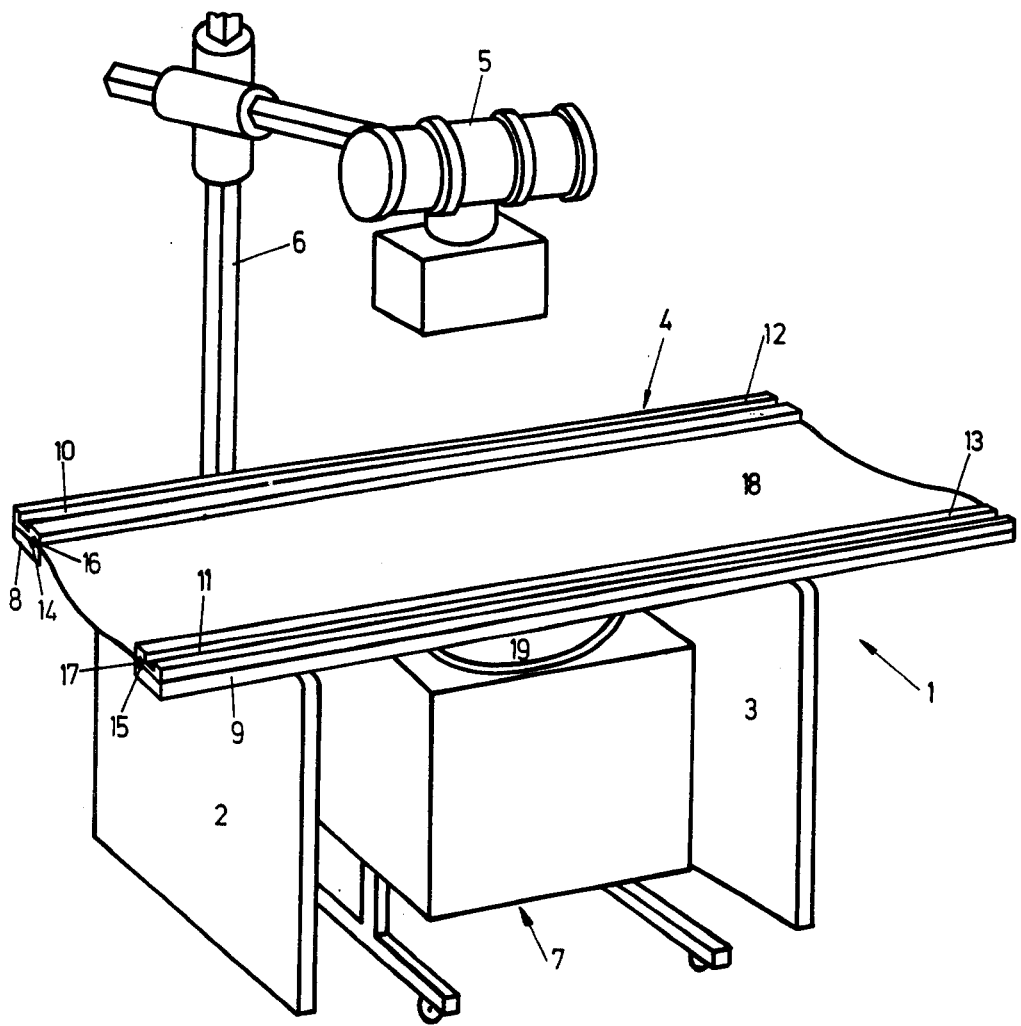
FIG. 1 is a perspective view of an X-ray apparatus with a patient support and an X-ray image amplifier.

FIG. 1 shows an X-ray apparatus as it is preferably used in medical diagnosis. An X-ray tube 5 is located above a patient support 1 having two legs 2 and 3 and a patient supporting top 4 mounted upon the legs and movable in two directions. The X-ray tube 5 is supported upon a stand 6 which is movable along the patient support. This apparatus has as its exposure device an X-ray image amplifier located in a casing 7 movably placed under the patient support. The patient supporting top has two longitudinal bars 8 and 9 upon which are screwed ledges 12 and 13 provided with grooves 10 and 11 for attaching corresponding parts. Upon the sides of the bars and their ledges located on top of each other are grooves 14, 15 extending in the longitudinal direction of the bars. Bead-like thickened parts 16, 17 of the edges of the supporting surface 18 are fixed in these grooves. The supporting surface consisting entirely of epoxyde synthetic resin strengthened with carbonic fibrous material hangs easily between the two bars. The side of the casing of the X-ray image amplifier directed toward the X-ray tube 5 is also provided with a cover 19 of epoxyde synthetic resin strengthened with carbonic fibrous material.

As already stated, all known epoxyde resins can be used. By way of example, polyphenylene is strengthened with any suitable carbonic fibres in a so-called "leaky mould" technique wherein an excess of resin is initially placed in a mould and then a weighed amount of fibres is added which become saturated. Another known method is called "pre-preg". It is a dry lay-up method wherein a dilute solution is used and the solvent is allowed to evaporate. These methods are described at length in an article entitled "Carbon-fibre — reinforced plastics" by I. N. Phillips, published in Transactions J. Plastics Inst. of August 1967.

Besides polyphenyllne it is possible to use polyester, epoxy phenolic, Fridel-Crafts. polyimide systems, Araldite, Devron, Epon, Epikote, Metallon, Scurol and all other epoxyde resins.

Epoxyde synthetic resin strengthened with carbonic fibrous material has a tensile strength corresponding to that of steel. When the supporting surface 16 is tensioned between the bars 8, 9 the synthetic material when loaded by a lying patient will be subjected substantially only to traction particularly when the supporting surface is slightly curved downwardly. This curvature takes also better in consideration the anatomic conditions of the patient's body. If in addition the traction is also uniformly transmitted to the longitudinal edges of the supporting surface 16 due to the bead-like formation and the fastening between the ledges and the bars then all requirements are provided to use a material, which anyway has a small X-ray absoration, with very thin walls and thus to attain an additional diminution of X-ray absorption. Along with the reduction of the X-ray absorption proceeds a further reduction of the stray rays produced in the material of the supporting surface. Since the side of the X-ray image amplifying casing directed to the X-ray tube is made of epoxide synthetic resin strengthened with carbonic fibrous material with the use of wall thicknesses such as were necessary for strength reasons for steel, it is also possible to provide here a minimum X-ray absorption and minimum stray rays.

Figure 2:
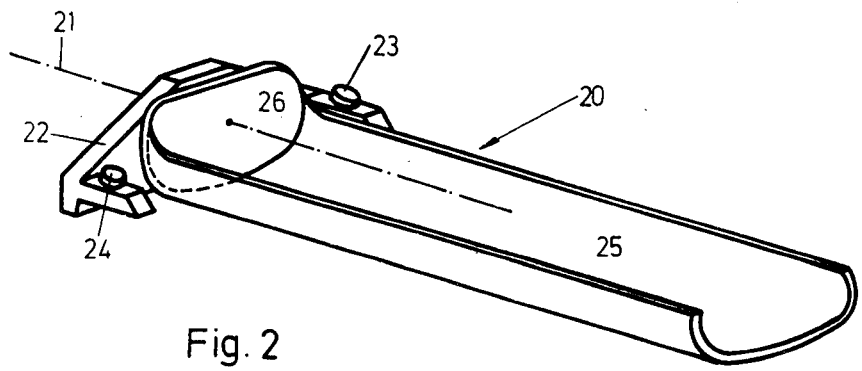
FIG. 2 is a perspective view of a patient supporting table top rotatable about its longitudinal axis.

FIG. 2 shows a patient supporting table top have the shape of a so-called rotary trough 20 which is mounted upon a bearing stand 22 so as to be swingable about its longitudinal axis 21. The supporting top can be fixed separately upon the ledges 12, 13 of an X-ray device corresponding to the illustration of FIG. 1 by means of fixing screws 23, 24. Due to its curved shape the trough-like body 25 not only provides for the patient a side support when swung, but also has a natural shape rigidity. The rigidity of the trough-like body is increased in the range of a foot plate 26 serving as a carrier for the support (not shown) when the curvature of the trough-like body is continuously transmitted to that of the foot plate without nitches. By using epoxyde synthetic resin strengthened with carbonic fibrous material a rotary trough-like body is produced having an extremely low X-ray absorption.

FIG. 3 shows in perspective, partly broken off, a patient supporting table top 27 as a compound structure, wherein the space between upper and lower covering layers 28, 29 is filled with hard foam 30. The upper and lower coverings are interconnected at the longitudinal edges of the supporting top have a practically triangular cross-section. The core of hard foam is glued to the two covering layers. This structure of a patient supporting top provides an exceptionally rigid body which as an exceptionally small X-ray absorption due to the use of hard foam and due to the high tensile strength of very thin upper and lower covering layers consisting of epoxyde synthetic resin strengthened with carbonic fibrous material. This construction is equally good for use in X-ray diagnosis and in ray therapy, and equally good for X-rays and gamma rays of radio isotopes.

FIG. 4 shows a conventional X-ray examining apparatus 31 having a patient supporting table top 32 capable of tipping upon one side of which is located an X-ray tube 33 and on the other side is an X-ray aiming device 34 movable jointly with the X-ray tube. Upon the side of the X-ray aiming device directed toward the table top is a part 35 of the casing of the aiming device located opposite a luminous screen (not shown) mounted with the aiming device. Thus the part 35 is struck by X-rays and is made of a plate of epoxyde synthetic resin strengthened with carbonic fibrous material. In this manner the X-ray absorption caused by the rear covering of the aiming device is greatly reduced as compared to conventional constructions.

Finally FIG. 5 shows an X-ray film cassette 36 consisting of two collapsible halves 37, 38. The half 38 directed to the X-ray source and indicated by a cross in the drawing is made of epoxyde synthetic resin strengthened with carbonic fibrous material. As compared to conventionally produced X-ray film cassette, this cassette has much better ray transmitting properties while having the same mechanical strength.

What is claimed is:

1. For the transmission of X-rays in medical X-ray examination and therapy devices, the use of carbon fiber tissue embedded in epoxy synthetic resin matrices for the patients table top, for the side of the casing of the X-ray image-intensifier directed toward the source of the X-rays, for the side of the casing of the X-ray spotfilm device directed toward the source of the X-rays and for the sides of cassettes directed toward the source of the X-rays.

2. An X-ray device according to claim 1 having a patient's table top manufactured by epoxy resins strengthened with carbon-fibers.

3. An X-ray device according to claim 2 having a patient's table top with a plate manufactured of epoxy resins strengthened with carbon-fibers, said plate being stretched between longitudinal bars of said table top.

4. An X-ray device according to claim 3, wherein said bars have grooves and wherein the longitudinal edges of said plate have head-like thickened parts fixed in said grooves.

5. An X-ray device according to claim 1, having a table top manufactured of top and bottom covering layers having a core of hard foam engaged between said layers, said layers being manufactured by resins strengthened with carbon-fibers.

6. An X-ray device according to claim 5 wherein said top and bottom layers are interconnected at least at the longitudinal sides of the table top.

7. An X-ray device according to claim 1 having the side of an X-ray image amplifying casing directed toward the source of X-rays manufactured by epoxy resins strengthened with carbon-fibers.

8. An X-ray device according to claim 1 having the side of the casing of an X-ray spotfilm directed toward the source of X-rays manufactured by epoxy resins strengthened with carbon-fibers.

9. An X-ray device according to claim 1 having X-ray film cassettes, the side of said cassettes directed toward the source of X-rays being manufactured by epoxy resins strengthened with carbon-fibers.

10. A process for X-ray examination and X-ray therapy wherein the ray dose being applied is diminished and using an X-ray examination and therapy device having parts which are penetrated by the rays and are subjected to high mechanical loads, said parts being composed of a material built from epoxy resin which is strengthened by inserted carbon fibers.

11. A casing of an image intensifier having a side directed toward a source of X-rays, said side consisting of a carbon fiber tissue embedded in an epoxy resin.

12. A casing of an X-ray spotfilm device having a side directed toward a source of X-rays, said side consisting of a carbon fiber tissue embedded in an epoxy resin.

13. An X-ray cassette having a side directed toward a source of X-rays, said side consisting of a carbon fiber tissue embedded in an epoxy resin.

* * * * *

REEXAMINATION CERTIFICATE (315th)

United States Patent [19]

Bergstrom et al.

[11] B1 4,146,793

[45] Certificate Issued Mar. 19, 1985

[54] X-RAY DEVICES USING EPOXY RESINS STRENGTHENED WITH CARBONIC FIBROUS MATERIAL

[75] Inventors: Lennart Bergstrom, Taby; Hans E. Warden, Upplands Vasby, both of Sweden

[73] Assignee: Siemens AG, Munich, Fed. Rep. of Germany

Reexamination Request:
No. 90/000,505, Feb. 15, 1984

Reexamination Certificate for:
Patent No.: 4,146,793
Issued: Mar. 27, 1979
Appl. No.: 675,785
Filed: Apr. 12, 1976

Related U.S. Application Data

[60] Continuation-in-part of Ser. No. 522,229, Nov. 8, 1974, abandoned, which is a division of Ser. No. 382,013, Jul. 23, 1973, abandoned.

[30] Foreign Application Priority Data

Jul. 27, 1972 [DE] Fed. Rep. of Germany ....... 2236942

[51] Int. Cl.³ ............................................. G03B 41/16
[52] U.S. Cl. ................................. 378/161; 378/176; 378/182; 378/208
[58] Field of Search .............. 378/161, 182, 208, 209, 378/169, 176

[56] References Cited

U.S. PATENT DOCUMENTS

| | | | |
|---|---|---|---|
| 1,925,425 | 9/1933 | Wilent | 250/444 |
| 2,922,047 | 1/1960 | Tour | 250/475 |
| 2,930,305 | 3/1960 | Sullivan | 250/475 |
| 3,108,018 | 10/1963 | Lewis | 117/161 |
| 3,157,787 | 11/1964 | Kendziorski, Jr. et al. | 250/68 |
| 3,159,524 | 12/1964 | Cantabene et al. | 161/58 |
| 3,281,598 | 10/1966 | Hollstein | 250/57 |
| 3,412,062 | 11/1968 | Johnson et al. | 260/37 |
| 3,449,570 | 6/1969 | Kok | 250/439 |
| 3,476,703 | 11/1969 | Wadsworth et al. | 260/37 EP |
| 3,598,693 | 8/1971 | Andersen et al. | 260/37 EP X |
| 3,627,466 | 12/1971 | Steingiser et al. | 260/37 EP X |
| 3,642,513 | 2/1972 | Sach et al. | 260/37 EP |
| 3,897,345 | 7/1975 | Foster | 250/439 |
| 3,947,686 | 3/1976 | Cooper et al. | 250/439 |

FOREIGN PATENT DOCUMENTS

| | | |
|---|---|---|
| 688786 | 4/1967 | Belgium . |
| 1637214 | 9/1951 | Fed. Rep. of Germany . |
| 1708184 | 7/1955 | Fed. Rep. of Germany . |
| 1039192 | 9/1958 | Fed. Rep. of Germany . |
| 1861111 | 9/1961 | Fed. Rep. of Germany . |
| 1219625 | 6/1966 | Fed. Rep. of Germany . |
| 1566126 | 8/1972 | Fed. Rep. of Germany . |
| 1430431 | 1/1966 | France . |
| 2110690 | 6/1972 | France . |
| 15775 | 11/1968 | Sweden . |
| 450622 | 4/1968 | Switzerland . |
| 1383212 | 2/1975 | United Kingdom . |
| 1385352 | 2/1975 | United Kingdom . |

OTHER PUBLICATIONS

Phillips; "Carbon-Fibre-Reinforced Plastics", Trans. J. Platics Inst., Aug. 1967, pp. 589-593.
"CARBOFORM®-Preimpregnated High Performance Carbon", Fothergill & Harvey Ltd., Pub. Nos. 27B, 33A and 36, 1971.
Phillips; "Carbon Fibres for Engineering Application-Part 2, The Introduction of Carbon Fibres Reinforced Plastics as a New Engineering Material", Proc. Inst. Mech. Engrs., vol. 185 52/71, 1971, pp. 793-806.
Kogyo Zairyo, vol. 18, No. 11, (1970-10), pp. 73-77 with German language Abstract and English translation of Abstract.
"Information Paper of the British House at Expo '70" received by Japanese Patent Office Sep. 1970 with German language abstract (English translation of German language abstract).
Physical Aspects of Irradiation, National Bureau of Standards Handbook 85, Mar. 31, 1964, p. 3.
Manley et al, "Lightweight Carbon Fibre Structures--Their Practical Use in Ballistocardiography, Composites, Mar. 1973.
Encyclopaedia Britannica, "X-Rays", vol. 23, (1968), pp. 846 and 852-855.
"Periodic Chart of the Elements", Fisher Scientific Company, 1973.

Primary Examiner—B. C. Anderson

[57] ABSTRACT

Cast resins strengthened with carbonic fibrous material are used as the material for making parts which transmit X-rays and at the same time are subject to mechanical stresses.

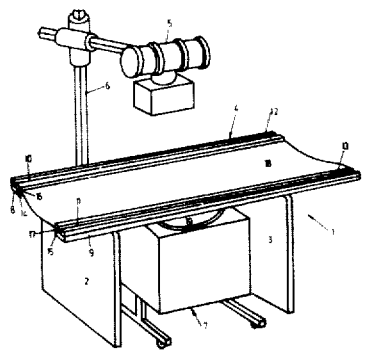

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–13 is confirmed.

New claims 14 and 15 are added and determined to be patentable.

*14. A patient table top for transmission of X-rays in medical X-ray examinations and therapy devices, said table top being constructed of material consisting of carbon fibers embedded in an epoxy resin.*

*15. For the transmission of X-rays in medical X-ray examinations and therapy devices, the use of carbon fibers embedded in an epoxy synthetic resin matrix for at least one of the following selected from a patient table top, a side of the casing of a X-ray image-intensifier directed toward the source of the X-rays, a side of the casing of a X-ray spot-film device directed toward the source of the X-rays and sides of cassettes directed toward the source of the X-rays.*